United States Patent
Keusenkothen et al.

(10) Patent No.: US 9,815,749 B2
(45) Date of Patent: Nov. 14, 2017

(54) HYDROCARBON DEHYDROCYCLIZATION

(71) Applicant: ExxonMobil Chemical Patents Inc., Baytown, TX (US)

(72) Inventors: Paul F. Keusenkothen, Houston, TX (US); Mohsen N. Harandi, The Woodlands, TX (US); John S. Buchanan, Flemington, NJ (US); Mayank Shekhar, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 15/240,830

(22) Filed: Aug. 18, 2016

(65) Prior Publication Data

US 2017/0144947 A1    May 25, 2017

Related U.S. Application Data

(60) Provisional application No. 62/326,918, filed on Apr. 25, 2016, provisional application No. 62/232,609, filed on Sep. 25, 2015.

(30) Foreign Application Priority Data

Nov. 19, 2015  (EP) ..................................... 15195311
Jun. 20, 2016  (EP) ..................................... 16175163

(51) Int. Cl.
*C07C 2/76*    (2006.01)
*C07C 2/64*    (2006.01)
(Continued)

(52) U.S. Cl.
CPC ................ *C07C 2/76* (2013.01); *C07C 1/20* (2013.01); *C07C 2/64* (2013.01); *C07C 2/78* (2013.01); *C07C 2/82* (2013.01)

(58) Field of Classification Search
None
See application file for complete search history.

(56) References Cited

U.S. PATENT DOCUMENTS

| 3,960,978 A | 6/1976 | Givens et al. |
| 4,016,218 A | 4/1977 | Haag et al. |

(Continued)

FOREIGN PATENT DOCUMENTS

| EP | 1 741 691 | 1/2007 |
| WO | 2010/140005 | 12/2010 |

(Continued)

OTHER PUBLICATIONS

Sattler et al., "Catalytic Dehydrogenation of Light Alkanes on Metals and Metal Oxides," Chem. Rev., 2014, vol. 114 (20), pp. 10613-10653.

(Continued)

*Primary Examiner* — Tam M Nguyen

(57) ABSTRACT

The invention relates to the production of aromatic hydrocarbon by the conversion of a feed comprising saturated hydrocarbon. At least a portion of the saturated hydrocarbon is converted to olefinic hydrocarbon. Aromatic hydrocarbon is produced from at least a portion of the olefinic hydrocarbon using at least one dehydrocyclization catalyst comprising dehydrogenation and molecular sieve components.

30 Claims, 1 Drawing Sheet

(51) Int. Cl.
*C07C 2/78* (2006.01)
*C07C 2/82* (2006.01)
*C07C 1/20* (2006.01)

(56) References Cited

U.S. PATENT DOCUMENTS

| | | | |
|---|---|---|---|
| 4,021,502 | A | 5/1977 | Plank et al. |
| 4,150,062 | A | 4/1979 | Garwood et al. |
| 4,227,992 | A | 10/1980 | Garwood et al. |
| 4,456,781 | A | 6/1984 | Marsh et al. |
| 4,751,338 | A | 6/1988 | Tabak et al. |
| 4,855,522 | A | 8/1989 | Diaz |
| 5,026,937 | A | 6/1991 | Bricker |
| 5,336,825 | A | 8/1994 | Choudhary et al. |
| 5,633,417 | A | 5/1997 | Beck et al. |
| 5,675,047 | A | 10/1997 | Beck et al. |
| 5,936,135 | A | 8/1999 | Choudhary et al. |
| 6,518,475 | B2 | 2/2003 | Fung et al. |
| 6,642,426 | B1 | 11/2003 | Johnson et al. |
| 6,670,517 | B1 | 12/2003 | Abichandani et al. |
| 7,015,369 | B2 | 3/2006 | Hack et al. |
| 7,357,872 | B2 | 4/2008 | Bratten |
| 7,846,401 | B2 | 12/2010 | Hershkowitz et al. |
| 8,692,043 | B2 | 4/2014 | Lauritzen et al. |
| 8,754,276 | B2 | 6/2014 | Buchanan et al. |
| 8,835,706 | B2 | 9/2014 | Iyer et al. |
| 9,144,790 | B2 | 9/2015 | Lauritzen et al. |
| 9,187,382 | B2 | 11/2015 | Hershkowitz et al. |
| 9,260,361 | B2 | 2/2016 | Keusenkothen et al. |
| 2005/0107481 | A1 | 5/2005 | Janssen et al. |
| 2007/0259972 | A1 | 11/2007 | Lattner et al. |
| 2008/0033218 | A1 | 2/2008 | Lattner et al. |
| 2009/0156870 | A1 | 6/2009 | Lauritzen et al. |
| 2009/0209794 | A1 | 8/2009 | Lauritzen et al. |
| 2014/0257001 | A1 | 9/2014 | Spicer et al. |
| 2015/0105597 | A1* | 4/2015 | Garza ............... C07C 2/865 585/437 |
| 2015/0190773 | A1* | 7/2015 | Chewter ............ B01J 38/02 585/312 |
| 2015/0368572 | A1 | 12/2015 | Rajagopalan et al. |
| 2015/0376088 | A1 | 12/2015 | Molinier et al. |
| 2017/0088490 | A1* | 3/2017 | Chen ............... C07C 5/3335 |
| 2017/0088492 | A1* | 3/2017 | Keusenkothen ........ C07C 5/415 |

FOREIGN PATENT DOCUMENTS

| | | |
|---|---|---|
| WO | 2013/177661 | 12/2013 |
| WO | 2014/193492 | 12/2014 |
| WO | 2015/084573 | 6/2015 |

OTHER PUBLICATIONS

Kirk Othmer Encyclopedia of Chemical Technology, 4th ed. 1998, vol. 9, 439-442.

* cited by examiner

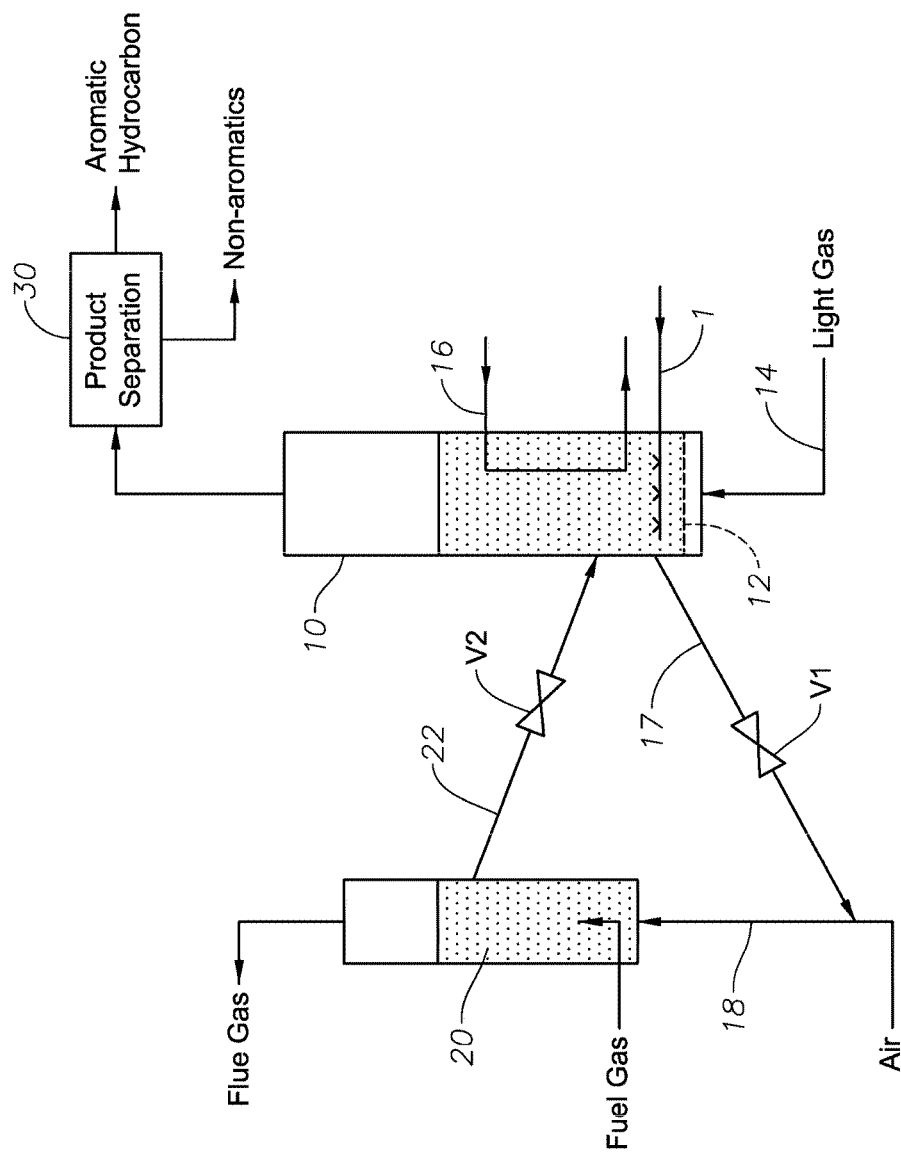

HYDROCARBON DEHYDROCYCLIZATION

CROSS-REFERENCE TO RELATED APPLICATIONS

This invention claims priority to and the benefit of U.S. Patent Application Ser. No. 62/326918, filed Apr. 25, 2016, European Patent Application No. 16175163.1, filed Jun. 20, 2016, U.S. Patent Application Ser. No. 62/232609, filed Sep. 25, 2015, and European Patent Application No. 15195311.4, filed Nov. 19, 2015, which are incorporated by reference herein in their entireties. The following related cases are also incorporated by reference in their entireties: U.S. Patent Application Ser. No. 62/234262, European Patent Application No. 15195314.8, U.S. Patent Application Ser. No. 62/234240, European Patent Application No. 15197698.2, U.S. Patent Application Ser. No. 62/248374, European Patent Application No. 15197702.2, U.S. Patent Application Ser. No. 62/253268, U.S. Patent Application Ser. No. 62/298655, European Patent Application No. 16167672.1, U.S. Patent Application Ser. No. 62/299730, European Patent Application No. 16167395.9, U.S. Patent Application Ser. No. 62/313288, European Patent Application No. 16173587.3, U.S. Patent Application Ser. No. 62/313306, European Patent Application No. 16173980.0, U.S. Patent Application Ser. No. 62/247795, filed Oct. 29, 2015 and European Patent Application No. 1519770.6.

FIELD

The invention relates to the production of aromatic hydrocarbon. A feed is converted to olefinic hydrocarbon, and aromatic hydrocarbon is produced from at least a portion of the olefinic hydrocarbon using at least one dehydrocyclization catalyst.

BACKGROUND

Aromatic hydrocarbon compounds such as benzene are frequently used for producing transportation fuels and petrochemicals such as styrene, phenol, nylon, polyurethanes and many others. Benzene can be produced, e.g., by steam cracking and naphtha reforming. During steam cracking, a $C_{2+}$ hydrocarbon feed reacts in the presence of steam under high-temperature pyrolysis conditions to produce a product comprising molecular hydrogen, $C_4$-olefin, other $C_4$-hydrocarbon, and $C_{5+}$ hydrocarbon. The yield of aromatic hydrocarbon from steam cracking is generally much less than the yield of light hydrocarbon, and processes of significant complexity are typically needed for aromatics separation and recovery. Naphtha reforming catalytically produces a product having a much greater content of aromatic hydrocarbon than does steam cracker effluent, but the naphtha feed is itself useful for other purposes such a as motor gasoline blendstock.

Attempts have been made to overcome these difficulties, and provide an efficient process for producing aromatic hydrocarbon at high yield from a relatively inexpensive feed. For example, processes have been developed for producing light aromatic hydrocarbon (e.g., benzene, toluene, and xylenes—"BTX") from paraffinic $C_1$-$C_4$ feeds. The processes typically utilize a catalyst having a molecular sieve component e.g., ZSM-5, and a dehydrogenation component, such as one or more of Pt, Ga, Zn, and Mo. These conventional processes typically operate at high temperature and low pressure. Although these conditions increase the yield of aromatic hydrocarbon, they also lead to an increased rate of catalyst deactivation, mainly resulting from increased catalyst coking.

One way to lessen the amount of catalyst coking involves increasing the relative amount of methane in the feed, as disclosed in U.S. Pat. No. 5,026,937. The relative amount of methane can be increased by removing $C_{2+}$ hydrocarbon from the feed. Since ethane, propane, and butanes are less refractory than methane, removing these compounds from the feed decreases the amount of over-cracking, and lessens the accumulation of catalyst coke.

Aromatization processes having a decreased selectivity for catalyst coke have also been developed. For example, U.S. Pat. No. 4,855,522 discloses using a dehydrocyclization catalyst comprising (a) an aluminosilicate having a silica : alumina molar ratio of at least 5 and (b) a compound of (i) Ga and (ii) at least one rare earth metal. The aromatization is carried out at a temperature ≥450° C. (e.g., 475° C. to 650° C.) and a pressure of from 1 bar to 20 bar. Other processes limit decrease selectivity for catalyst coke by carrying out the reaction for a relatively short time (e.g., less than a day), and then halting the reaction so that the catalyst can be regenerated. For example, U.S. Patent Application Publication No. 2009/0209794 A1, and U.S. Pat. Nos. 8,692,043 and 9,144,790 disclose a process for aromatizing lower alkanes such as ethane using a particulate catalyst, where the catalyst particles have an average catalyst particle residence time in the reaction zone in the range of about 0.1 second to about 30 minutes. According to those references, such a residence time can be achieved by carrying out the aromatization in a fluid bed, and continuously withdrawing catalyst from the bed for regeneration. Maximum ethane conversion is about 63%, and the catalyst and process conditions which achieve appreciable ethane conversion also exhibit appreciable selectivity for methane.

It is desired to produce aromatic hydrocarbon from saturated hydrocarbon at greater feed conversion, particularly with less methane yield. Processes which operate at a space velocity (GHSV) greater than 1000 $hr^{-1}$ are particularly desired, as are those which can utilize a feed comprising relatively refractory hydrocarbon such as methane.

SUMMARY

The invention is based in part on the development of catalytic processes for hydrocarbon aromatization which feature greater feed conversion and typically less methane selectivity than conventional aromatization processes. The process can utilize feeds comprising hydrocarbon, e.g., one or more of $C_{5+}$ hydrocarbon; substantially non-aromatic hydrocarbon; and substantially saturated hydrocarbon, including paraffinic hydrocarbon, such as methane. The processes include converting at least a portion of the feed's hydrocarbon to olefinic hydrocarbon. The olefinic hydrocarbon is exposed to at least one dehydrocyclization catalyst under catalytic dehydrocyclization conditions to convert at least a portion of the olefin to aromatics.

Surprisingly, it has been found that a significant yield of aromatic hydrocarbon can be obtained during the olefin conversion step, without excessive yield of saturated light hydrocarbon, when the average residence time of the dehydrocyclization catalyst in the reaction zone under reaction conditions is about 90 seconds or less. Accordingly, certain aspects of the invention relate to a process for producing aromatic hydrocarbon from a feed comprising paraffinic hydrocarbon such as ≥1 wt. % of methane. During an olefin production step, an olefinic product is produced by converting ≥10 wt. % of the feed's paraffinic hydrocarbon to $C_2$-$C_4$ olefinic hydrocarbon in a first conversion zone, wherein the olefinic product includes at least portion of the $C_2$-$C_4$ olefinic hydrocarbon. An aromatic product is produced from the olefinic hydrocarbon during an olefin conversion step. During the olefin conversion step, ≥10 wt. % of the olefinic product's $C_2$-$C_4$ olefinic hydrocarbon is converted to aromatic hydrocarbon in a second conversion zone in the presence of a dehydrocyclization catalyst to produce the aromatic product. The dehydrocyclization catalyst includes a molecular sieve component and a dehydrogenation component, and has catalytic activity for hydrocarbon dehydrocyclization. The dehydrocyclization catalyst has an average residence time in the conversion zone under the conversion conditions of ≤90 seconds. The olefin conversion step is carried out under conversion conditions which include a temperature in the range of from 400° C. to 700° C., a pressure in the range of from 0 psig (101 kPa) to 300 psig (2170 kPa). The process also includes recovering aromatic hydrocarbon from the aromatic product.

It has also been found that carrying out the olefin conversion step in a turbulent fluidized bed also results in an improved yield of aromatic hydrocarbon. Accordingly, in other aspects the invention relates producing an olefinic product in an olefin production step by converting a feed comprising paraffinic hydrocarbon. An olefinic product is produced during the olefin production step by converting ≥10 wt. % of the feed's paraffinic hydrocarbon to $C_2$-$C_4$ olefinic hydrocarbon in a first conversion zone, wherein the olefinic product includes at least portion of the $C_2$-$C_4$ olefinic hydrocarbon. An aromatic product is produced during an olefin conversion step by converting ≥10 wt. % of the olefinic product's $C_2$-$C_4$ olefinic hydrocarbon to aromatic hydrocarbon in the presence of the fluidized catalyst in a second conversion zone, the fluidized catalyst having catalytic activity for hydrocarbon dehydrocyclization. The olefin conversion is carried out under turbulent fluidized bed conversion conditions which include a temperature in the range of from 400° C. to 700° C., a pressure in the range of from 0 psig (101 kPa) to 300 psig (2170 kPa), and the aromatic product includes at least a portion of the aromatic hydrocarbon. The process also includes recovering aromatic hydrocarbon from the aromatic product.

In other aspects, the invention relates to one or more systems or apparatus for carrying any of the preceding processes.

BRIEF DESCRIPTION OF THE FIGURES

The FIGURE is a schematic representation of certain aspects of the invention in which the dehydrocyclization reaction is carried out in a fluidized bed.

DETAILED DESCRIPTION

The invention relates to hydrocarbon upgrading by producing desirable aromatic hydrocarbon from feeds of lesser value. The processes include converting at least a portion of the feed's hydrocarbon to olefinic hydrocarbon. The olefinic hydrocarbon is exposed to at least one dehydrocyclization catalyst under catalytic dehydrocyclization conditions to convert at least a portion of the olefinic hydrocarbon to aromatic hydrocarbon, particularly $C_{11-}$ aromatic hydrocarbon, and more particularly BTX. For the purpose of this description and dependent claims, the following terms are defined.

The term "$C_n$" hydrocarbon means hydrocarbon having n carbon atom(s) per molecule, wherein n is a positive integer. The term "$C_{n+}$" hydrocarbon means hydrocarbon having at least n carbon atom(s) per molecule. The term "$C_{n-}$" hydrocarbon means hydrocarbon having no more than n carbon atom(s) per molecule. The term "hydrocarbon" means a class of compounds containing hydrogen bound to carbon, and encompasses (i) saturated hydrocarbon, (ii) unsaturated hydrocarbon, (iii) mixtures of hydrocarbons, and including mixtures of hydrocarbon compounds (saturated and/or unsaturated) having different values of n.

The terms "alkane" and "paraffinic hydrocarbon" mean substantially-saturated compounds containing hydrogen and carbon only, e.g., those containing ≤1% (molar basis) of unsaturated carbon atoms. As an example, the term alkane encompasses $C_2$ to $C_{20}$ linear, iso, and cyclo-alkanes. Aliphatic hydrocarbon means hydrocarbon that is substantially free of hydrocarbon compounds having carbon atoms arranged in one or more rings.

The term "unsaturate" and "unsaturated hydrocarbon" refer to one or more $C_{2+}$ hydrocarbon compounds which contain at least one carbon atom directly bound to another carbon atom by a double or triple bond. The term "olefin" and "olefinic hydrocarbon" refer to one or more unsaturated hydrocarbon compound containing at least one carbon atom directly bound to another carbon atom by a double bond. In other words, an olefin is a compound which contains at least one pair of carbon atoms, where the first and second carbon atoms of the pair are directly linked by a double bond. The term "aromatics" and "aromatic hydrocarbon" mean hydrocarbon compounds containing at least one aromatic ring. Non-aromatic hydrocarbon is hydrocarbon comprising ≤1 wt. % of carbon atoms included in aromatic rings. Non-olefinic hydrocarbon is hydrocarbon comprising ≤1 wt. % of olefin. Substantially saturated hydrocarbon contains ≤1 wt. % of olefin and ≤1 wt. % of aromatics.

The term "Periodic Table" means the Periodic Chart of the Elements, as it appears on the inside cover of The Merck Index, Twelfth Edition, Merck & Co., Inc., 1996.

"Dehydrocyclization" means removing hydrogen from and cyclizing a non-cyclic hydrocarbon to produce aromatic hydrocarbon and typically (i) cyclo-paraffin and/or (ii) cyclo-olefin. Dehydrocyclization can be carried out in one step which includes both dehydrogenation and cyclization. Dehydrocyclization can be carried out in one step, in two steps, e.g., dehydrogenation followed by cyclization of the dehydrogenated intermediate; or in three or more steps, e.g., normal paraffin dehydrogenation, cyclization of the olefinic intermediate, and additional dehydrogenation (aromatization) of the cyclo-olefin intermediate. The dehydrocyclization (including any dehydrogenation carried out in connection with dehydrocyclization) is "non-oxidative" meaning that the reaction is carried out with little if any oxidative coupling of feed hydrocarbon, intermediate hydrocarbon (if any), or dehydrocyclization product.

The terms "reaction zone" or "reactor zone" mean a location within a reactor, e.g., a specific volume within a reactor, for carrying out a specified reaction. A reactor or reaction stage can encompass one or more reaction zones. More than one reaction can be carried out in a reactor, reactor stage, or reaction zone. For example, a reaction stage can include a first zone for carrying out first and second reactions and a second zone for carrying out a third reaction, where the first reaction (e.g., dehydrocyclization) can be the same as or different from the second reaction, and the third reaction (e.g., $CO_2$ methanation) can be the same as or different from the second reaction. When the reaction zone contains catalyst, the reaction can feature an average residence time of the catalyst in the reaction zone under the reaction conditions. The catalyst can, e.g., reside in a fixed catalyst bed located in a zone of a reactor. In these configurations, the zone is a reaction zone when the catalyst is exposed to the desired feed under the desired reaction conditions (reaction mode). The zone is a regeneration zone when the catalyst is exposed to a regenerating medium (e.g., air) under catalyst regeneration conditions (regeneration mode). These configurations can be operated continuously by switching between reaction mode and regeneration mode cyclically (e.g., in sequence). In these configurations, the average residence time is the average time the catalyst in the zone is exposed to the desired feed and the desired reaction conditions, e.g., the average time between the start of reaction mode operation and the start of regeneration mode operation, such as the average duration of reaction mode operation. For typical catalyst beds, the average residence time is the time period from (i) the time at which a bed of fresh or freshly regenerated catalyst is first exposed to the specified catalytic dehydrocyclization conditions to (ii) the time at which the catalyst bed is removed from dehydrocyclization service, e.g., for replacement and/or regeneration. A fixed catalyst bed can be removed from dehydrocyclization service by, e.g., discontinuing feed flow and/or exposing the bed to conditions other than the specified dehydrocyclization conditions. In cyclic operation over repeated reaction and regeneration modes, the time period is numerically averaged over the number of cycles. In other configurations, a reaction zone and regeneration zone operate at the same time, e.g., in separate vessels. For example, a first bed of catalyst particles can be located in the reaction zone, with a second bed of catalyst particles located in the regeneration zone. Catalyst particles withdrawn from the reaction zone bed can be transferred to the regeneration zone's bed for regeneration. In typically fluidized bed operation, the catalyst is removed from dehydrocyclization service by gradually withdrawing catalyst particles from the bed at a mass flow rate $MFR_1$ until 100% of the bed's mass ("M") is removed. In these aspects, the average time period is the average amount of time needed to remove 100% of the bed's catalyst particles, e.g., [$M/MFR_1$].

The term "selectivity" refers to the production (on a weight basis) of a specified compound in a catalytic reaction. As an example, the phrase "a light hydrocarbon conversion reaction has 100% selectivity for aromatic hydrocarbon" means that 100% of the light hydrocarbon (weight basis) that is converted in the reaction is converted to aromatic hydrocarbon. When used in connection with a specified reactant, the term "conversion" means the amount of the reactant (weight basis) consumed in the reaction. For example, when the specified reactant is $C_4$ paraffinic hydrocarbon, 100% conversion means 100% of the $C_4$ paraffinic hydrocarbon is consumed in the reaction. Yield (weight basis) is conversion times selectivity.

Certain hydrocarbon feeds useful for the dehydrocyclization will now be described in more detail. The invention is not limited to these feeds, and this description is not meant to foreclose the use of other feeds within the broader scope of the invention.

Representative Feeds

An advantage of the invention is that it encompasses a wide range of hydrocarbon-containing feeds, and is particularly suitable for use with refractory feeds such as methane and residual hydrocarbon such as atmospheric resid and/or vacuum resid. For example, the feed can comprise hydrocarbon having a hydrogen content (i) in the range of 6.0 wt. % to 25.0 wt. %, 8.0 wt. % to 20.0 wt. %, or (ii) in the range of 20.0 wt. % to 25.0 wt. %. Hydrogen content is determined in accordance with ASTM D4808-01 (2006). The feed can be one that is derived from petroleum and/or coal deposits; e.g., those having one or more of the following properties: a Conradson Carbon amount in the range of 5 wt. % to 40 wt. %, an API Gravity in the range of from −10° to 35°, and a boiling point at atmospheric pressure ≥340° C., e.g., ≥650° C. Typically, the feed comprises a total of ≤10 wt.% of impurities such as CO, $CO_2$, $H_2S$, and total mercaptan; e.g., ≤1 wt. %, or ≤0.1 wt.%. It is also typical for the feed to contain ≤10 wt. % of $C_2$-$C_{10}$ unsaturated hydrocarbon compounds, e.g., ≤1 wt.%, or ≤0.1 wt.%. More typically, the feed is substantially free of (i) $C_2$-$C_5$ olefinic hydrocarbon compounds and/or (ii) $C_6$-$C_{10}$ aromatic hydrocarbon compounds (particularly BTX). The feed can comprise non-olefinic hydrocarbon and/or non-aromatic hydrocarbon. For example, the feed can comprise substantially-saturated hydrocarbon.

In certain aspects, the feed (a "First Feed") comprises ≥1 wt. % methane, e.g., ≥5 wt. % methane, such as ≥10 wt. %, or ≥25 wt. %, or ≥50 wt. %, or ≥75 wt. %, or ≥90 wt. %, based on the weight of the feed. For example, the hydrocarbon feed can comprise 5 wt. % to 99 wt. % methane, such as 10 wt. % to 95 wt. % methane. Optionally, the feed further comprises additional hydrocarbon, typically additional non-aromatic hydrocarbon, more typically additional saturated hydrocarbon. For example, the feed can further comprise one or more $C_2$ to $C_9$ non-aromatic, non-olefinic hydrocarbon compounds, e.g., one or more light paraffinic hydrocarbon (i.e., $C_2$ to $C_5$) compounds, and particularly one or more $C_2$-$C_4$ normal and/or iso-paraffinic hydrocarbon compounds. Suitable feeds include those which comprise methane and further comprise ≥1 wt. % of one or more of (i) paraffinic $C_2$ to $C_9$ hydrocarbon, (ii) aliphatic paraffinic $C_2$ to $C_9$ hydrocarbon, (iii) paraffinic light hydrocarbon, and (iv) aliphatic paraffinic light hydrocarbon; such as ≥10 wt. %, or ≥25 wt. %, or ≥50 wt. %, or ≥75 wt. %, or ≥90 wt. %. One representative feed comprises 1 wt. % to 40 wt. % methane, 10 wt. % to 40 wt. % ethane, 20 wt. % to 50 wt. % propane, 20 wt. % to 50 wt. % butanes and ≤1 9wt. % of non-paraffinic hydrocarbon. Suitable methane-containing feeds are described in U.S. Pat. No. 7,846,401, which is incorporated by reference herein in its entirety.

In other aspects, the feed (a "Second Feed") comprises one or more $C_2$-$C_4$ paraffinic hydrocarbon compounds, e.g., ≥5 wt. % methane, such as ≥10 wt. %, or ≥25 wt. %, or ≥50 wt. %, or ≥75 wt. %, or ≥90 wt. %, based on the weight of the feed. For example, the hydrocarbon feed can comprise 5 wt. % to 99 wt. % of $C_2$-$C_4$ paraffinic hydrocarbon, such as 10 wt. % to 95 wt. % methane. Optionally, in these aspects, the feed further comprises additional hydrocarbon, e.g., one or more non-aromatic $C_5$-$C_9$ hydrocarbon compounds, such as one or more paraffinic $C_5$-$C_9$ hydrocarbon compounds. For example, the feed can further comprise ≥1 wt. % based on the weight of the feed of one or more of (i) non-aromatic $C_5$ to $C_9$ hydrocarbon, (ii) aliphatic $C_5$ to $C_9$ hydrocarbon, and (iii) aliphatic paraffinic $C_5$ to $C_9$ hydrocarbon, such as ≥10 wt. %, or ≥25 wt. %, or ≥50 wt. %, or ≥75 wt. %, or ≥90 wt. %. One representative feed comprises e.g., ≥50 wt. % ethane, such as ≥75 wt. %, or ≥90 wt. %, or ≥95 wt. %. For example, the feed can comprise an amount of ethane in the range of from 1 wt. % to 99 wt. %, such as 5 wt. % to 95 wt. %, or 10 wt. % to 90 wt. %. One representative feed comprises (i) ≥10 wt. % ethane, or ≥50 wt. %, or ≥90 wt. %, such as in the range of from 10 wt. % to 99.5 wt. % ethane, with ≥95 wt.% of the balance of the feed comprising one or more of methane, propane, and butanes. Although the feed of these aspects can contain $C_{5+}$ hydrocarbon, the amount of $C_{5+}$ hydrocarbon when present is typically small, e.g., ≤20 wt. %, such as ≤10 wt. %, or ≤1 wt. %. Typically, the feed contains ≤10 wt. % of $C_{6+}$ saturated hydrocarbon, e.g., ≤5 wt. %. Representative feeds are disclosed in U.S. Patent Application Publication No. 2014/0257001 A1, which is incorporated by reference herein in its entirety.

In other aspects, the feed (a "Third Feed") comprises one or more $C_{5+}$ saturated hydrocarbon compounds, e.g., relatively refractory hydrocarbon compounds such as resid. For example, suitable feeds of these aspects include one or more of gas oil, aromatic gas oil, steam cracked gas oil and residues, gas oils, heating oil, jet fuel, diesel, kerosene, gasoline, coker naphtha, steam cracked naphtha, catalytically cracked naphtha, hydrocrackate, reformate, raffinate reformate, Fischer-Tropsch liquids, Fischer-Tropsch gases, natural gasoline, distillate, virgin naphtha, atmospheric pipestill bottoms, vacuum pipestill streams including bottoms, wide boiling range naphtha to gas oil condensates, heavy non-virgin hydrocarbon streams from refineries, vacuum gas oils, heavy gas oil, naphtha contaminated with crude, atmospheric residue, heavy residue, $C_4$/residue admixture, naphtha/residue admixture, hydrocarbon gases/residue admixtures, hydrogen/residue admixtures, gas oil/residue admixture, crude oil, and reduced petroleum crude oil. Particular heavy oil feeds within the scope of the invention include pitch; asphalt; bitumen; other heavy hydrocarbon residues; tar sand oil; shale oil; or even a coal slurry or coal liquefaction product such as coal liquefaction bottoms. Such feeds typically have a Conradson Carbon Residue (ASTM D189-165) of at least 5 wt. %, generally from about 5 to 50 wt. %. Suitable Third Feeds are disclosed in U.S. Patent Application Publication No. 2015/0368572 A1, and U.S. Pat. Nos. 9,260,361, and 7,351,872, each of which being incorporated by reference herein in its entirety.

Mixtures comprising one or more of the First Feed, Second Feed, and Third Feed are within the scope of the invention. For example the feed can comprise (i) a methane-containing gas of synthetic and/or geological origin) and/or (ii) aromatic gas oil ("AGO"), wherein AGO means hydrocarbon having ≥1.0 wt. % of the hydrocarbon's carbon atoms included in an aromatic ring, e.g., 5.0 wt. %, such as 10.0 wt. %, based on the weight of the hydrocarbon.

An olefinic product comprising olefinic product's $C_2$-$C_4$ olefinic hydrocarbon is produced from one or more of the specified feeds. At least a portion of the olefinic product's $C_2$-$C_4$ olefinic hydrocarbon is exposed to at least one dehydrocyclization catalyst under dehydrocyclization conditions to convert at least a portion of the olefinic product's $C_2$-$C_4$ olefinic hydrocarbon to aromatic hydrocarbon. Certain aspects of the olefin production will now be described in more detail. The invention is not limited to these aspects, and this description is not meant to foreclose other aspects olefin production within the broader scope of the invention.

Representative Methods for Making Olefinic Hydrocarbon

At least one olefin production process is utilized for producing an olefinic product comprising $C_2$-$C_4$ olefinic hydrocarbon. Conventional olefin production methods can be used, but the invention is not limited thereto. The method of olefin production is typically selected for efficient conversion of the feed utilized.

For feeds such as the First Feed, the olefinic hydrocarbon can be produced by one or more of (i) high-temperature pyrolysis, (ii) oxidative and/or non-oxidative methane coupling, and (iii) methanol conversion to oxygenate and then conversion of the oxygenate to olefinic hydrocarbon using, e.g., oxygenate dehydration and/or other oxygenate-to-olefin processes. Suitable pyrolysis processes are disclosed in U.S. Pat. Nos. 7,846,401 and 9,187,383. Suitable oxidative methane coupling processes are described in U.S. Patent Application Publication No. 2014/0012053 A1, International Patent Application Publication No. WO 2103/177661 A1, and P.C.T. Patent Application Publication No.WO2015/031357, including references cited in one or more of these. Suitable oxygenate production/conversion processes are disclosed in (i) P.C.T. Patent Application Publication No. WO 2015/84573 A1, (ii) U.S. Patent Application Publications Nos. 2005/0107481 A1, 2008/0033218 A1, and 2007/0259972 A1, (iii) U.S. Pat. Nos. 7,015,369, 4,499,327, and 6,518,475, and (iv) references cited in these. All of the preceding references are incorporated by reference herein in their entirety.

For feeds such as the Second Feed, the olefinic hydrocarbon can be produced by one or more of (i) hydrocarbon pyrolysis, including hydrocarbon pyrolysis carried out in the presence of steam (steam cracking), (ii) oxidative and/or non-oxidative alkane coupling, e.g., using methods similar to those utilized with the First Feed, (iii) paraffin conversion to oxygenate and then conversion of the oxygenate to olefinic hydrocarbon, e. g., using methods similar to those utilized with the First Feed, and (iv) catalytic and non-catalytic alkane dehydrogenation including oxydehydrogenation and hydrogen transfer. Typical steam cracking processes include exposing a mixture of the Second Feed and water to a temperature in the range of about 600° C. to about 1100° C., a pressure in the range of about 1.5 to 2.75 bar, and a residence time in the range of 0.1 to 0.6 second. Suitable steam cracking processes are disclosed in U.S. Patent Application Publication No. 2014/0257001 A1, and in P.C.T. Patent Application Publication No. WO 2014/193492 A1. Suitable olefin production methods also include dehydrogenation processes, such as those described in European Patent Application Publication No. EP 1741691 A1, and in U.S. Pat. Nos. 9,260,361, 8,754,276, and 5,585,530. In particular, alkane dehydrogenation processes are described in Jesper et al., Catalytic Dehydrogenation of Light Alkanes on Metals and Metal Oxides, Chem. Rev., 2014, 114 (20), pp 10613-10653, and in references cited therein. All of the preceding references are incorporated by reference herein in their entirety.

Suitable processes for producing olefinic hydrocarbon from the Third Feed include (i) high temperature pyrolysis such as that used for processing the First Feed, (ii) catalytic cracking, and (iii) other forms of thermal conversion such as visbreaking and coking. Suitable methods are disclosed in, e.g., Kirk Othmer Encyclopedia of Chemical Technology, $4^{th}$ ed. 1998, Vol. 9, 439-442, and in U.S. Patent Application Publication No. 2015/0368572 A1, the contents of which are incorporated by reference herein in their entireties.

Among the foregoing processes, those which produce mainly $C_2$-$C_4$ olefinic hydrocarbon are particularly desired. For processes that produce a mixture of the desired $C_2$-$C_4$ olefinic hydrocarbon and (i) olefinic hydrocarbon having more than 4 carbon atoms, and/or (ii) non-olefin by-products (including unreacted feed), the desired $C_2$-$C_4$ olefinic hydrocarbon is typically separated for further processing in the dehydrocyclization step. In certain aspects, the olefin production process (i) operates at a higher temperature than does the dehydrocyclization and (ii) the olefin production process produces mainly $C_2$-$C_4$ olefinic hydrocarbon, e.g., ≥50 wt. % of $C_2$-$C_4$ olefinic hydrocarbon, or ≥75 wt. % , or ≥90 wt. %. In these aspects, the dehydrocyclization can be utilized for the additional purpose of quenching the olefinic product made by the olefin production step. Typically, the olefinic product of the olefin production step comprises ≤1 wt. % of aromatic hydrocarbon, e.g., ≤0.1 wt. %. More typically, the olefinic product of the olefin production step comprises ≤1 wt. % of $C_{10+}$ aromatic hydrocarbon, e.g., ≤0.1 wt. %.

An olefinic product typically comprising $C_2$-$C_4$ olefinic hydrocarbon is produced by the olefin production step. In some aspects, the desired olefinic product is produced directly, e.g., as in the case of propane dehydrogenation and/or oxidative methane coupling. In other aspects, the olefinic product is produced indirectly, e.g., as in the case when the olefin production step includes cracking such as steam cracking. In those aspects, an olefinic product comprising $C_2$-$C_4$ olefinic hydrocarbon is typically separated from other streams (e.g., saturated hydrocarbon) produced by the olefin production process. The olefinic product typically comprises ≥10 wt. % of $C_2$-$C_4$ olefinic hydrocarbon, e.g., ≥25 wt. %, such as ≥50 wt. %, or ≥75 wt. %, or ≥90 wt. %. For example, the olefinic product can comprise 1 wt. % to 99 of $C_2$-$C_4$ olefinic hydrocarbon, e.g., 10 wt. % to 95 wt. %, or 25 wt. % to 90 wt. %. Besides $C_2$-$C_4$ olefinic hydrocarbon, the olefinic product can contain one or more of diluent (e.g., inert gas such as molecular nitrogen and/or argon) and/or $C_1$-$C_4$ saturated hydrocarbon. The amounts of these, when present, are typically ≤25 wt. %, e.g., ≤10 wt. %, such as ≤1 wt. %. Since it adversely effects the yield of aromatic hydrocarbon, molecular hydrogen produced during the olefin production step can be separated and conducted away upstream of the aromatization step.

Aromatic hydrocarbon is produced by exposing at least a portion of the olefinic product's $C_2$-$C_4$ olefinic hydrocarbon to at least one dehydrocyclization catalyst under dehydrocyclization conditions. The dehydrocyclization catalyst has an average residence time in the reaction zone under the dehydrocyclization conditions of ≤90 seconds. Certain aspects of the dehydrocyclization catalyst will now be described in more detail. The invention is not limited to these aspects, and this description is not meant to foreclose other aspects of the dehydrocyclization catalyst within the broader scope of the invention.

Representative Dehydrocyclization Catalysts

Typically, the dehydrocyclization catalyst includes ≥10 wt. % of the molecular sieve component and ≥0.005 wt. % of the dehydrogenation component, wherein the molecular sieve component has a Constraint Index in the range of from 1-12, and the dehydrogenation component comprises one or more elements selected from Groups 3 to 13 of the Periodic Table. When the molecular sieve component and dehydrogenation component together include less than 100 wt. % of the catalyst, ≥90 wt. % of the remainder of the catalyst can include a matrix component, such as ≥99 wt. % of the remainder.

The catalyst typically includes the molecular sieve component in an amount ≥20 wt. %, based on the weight of the catalyst, e.g., ≥25 wt. %, such as ≥50 wt. %, or in the range of from 30 wt. % to 99.9 wt. %. In certain aspects, the molecular sieve component includes aluminosilicate, e.g., ≥90 wt. % of at least one aluminosilicate. The aluminosilicate can be an un-substituted aluminosilicate, a substituted aluminosilicate, or a combination thereof. For example, the aluminosilicate can be in a form where at least a portion of its original metal has been replaced, e.g., by ion exchange, with other suitable metal (typically metal cation) of Groups 1-13 of the Periodic Table. Typically, the aluminosilicate includes zeolite aluminosilicate, e.g., ≥90 wt. % of at least one zeolite based on the weight of the aluminosilicate. The term zeolite includes those in which at least part of the aluminum is replaced by a different trivalent metal, such as gallium or indium.

The molecular sieve component typically includes ≥90 wt. % of one or more of the specified molecular sieves, e.g., ≥95 wt. %. In certain aspects, the molecular sieve component includes at least one zeolite molecular sieve, e.g., ≥90 wt. % zeolite, such as ≥95 wt. %, based on the weight of the molecular sieve component. The molecular sieve component can consist essentially of zeolite, consist of zeolite, or can include zeolite in combination with other (e.g., non-zeolitic) molecular sieve. The zeolite can be in hydrogen form, e.g., zeolite synthesized in the alkali metal form and then converted to the hydrogen form. Typically the zeolite has a medium pore size and a Constraint Index of 2-12 (as defined in U.S. Pat. No. 4,016,218). Optionally, the zeolite has at least one set of pores of substantially uniform size extending through the molecular sieve, wherein geometric mean of the cross-sectional dimensions of each of the sets of pores is ≥5 Å, or ≥5.3 Å, e.g., ≥5.4 Å such as ≥5.5 Å, or in the range of 5 Å to 7 Å, or 5.4 Å to 7 Å. Examples of suitable zeolites include ZSM-5 (including H-ZSM-5), ZSM-11, ZSM-12, ZSM-22, ZSM-23, ZSM-35, and ZSM-48, including and mixtures and intermediates thereof such as ZSM-5/ZSM-11 admixture. For example, the molecular sieve component can include ≥90 wt. % of (A) ZSM-5 and/or (B) ZSM-12, based on the weight of the molecular sieve component, e.g., ≥95 wt. % of H-ZSM-5. In certain aspects, the molecular sieve has a relatively small crystal size, e.g., small crystal ZSM-5, meaning ZSM-5 having a crystal size ≤0.05 micrometers (μm), such as in the range of 0.02 μm to 0.05 μm. Small crystal ZSM-5 and the method for determining molecular sieve crystal size are disclosed in U.S. Pat. No. 6,670,517, which is incorporated by reference herein in its entirety.

In other aspects, the molecular sieve component includes at least one molecular sieve of the MCM-22 family (including mixtures of MCM-22 family molecular sieve), e.g., MCM-22 alone or in combination with other molecular sieve such as one or more of the specified zeolites. The MCM-22 family includes those molecular sieves having an X-ray diffraction pattern including d-spacing maxima (in A) at 12.4±0.25, 6.9±0.15, 3.57±0.07 and 3.42±0.07. Examples of suitable MCM-22-family molecular sieve include PSH-3, SSZ-25, ITQ-1, MCM-36, MCM-49, MCM-56, UZM-8, ERB-1, and ITQ-2.

When the molecular sieve component includes at least one aluminosilicate, the aluminosilicate's silica:alumina ratio (substantially the same as the aluminosilicate's $Si:Al_2$ atomic ratio) is typically ≥2, e.g., in the range of from 5 to 100. The silica:alumina ratio is meant to represent the $Si:Al_z$ atomic ratio in the rigid anionic framework of the crystalline aluminosilicate.

In addition to the molecular sieve component, the catalyst includes ≥0.005 wt. %, based on the weight of the catalyst, of a dehydrogenation component, such as, phosphorous and/or at least one dehydrogenation metal. For example, the dehydrogenation component can include one or more neutral metals selected from Groups 3 to 13 of the Periodic Table, such as one or more of Ga, In, Zn, Cu, Re, Mo, W, La, Fe, Ag, Pt, and Pd, and/or one or more oxides, sulfides and/or carbides of these metals. More particularly, the dehydrogenation component can be Ga, Zn, or a combination thereof, optionally supported on a catalyst including ZSM-5 as the molecular sieve component.

Typically, the dehydrogenation component includes ≥90 wt. % of the one or more of the specified dehydrogenation metals and/or oxide thereof, e.g., ≥95 wt. %, or ≥99 wt. %.

For example, the dehydrogenation component can include ≥90 wt. % of (A) Ga and/or (B) Zn, including oxides thereof. Typically, the catalyst includes ≥0.01 wt. % of the dehydrogenation component, based on the weight of the catalyst, e.g., ≥0.1 wt. % of the dehydrogenation component, such as ≥0.5 wt. %, or ≥1 wt. %.

Those skilled in the art will appreciate that when the dehydrogenation component includes one or more metals of greater catalytic dehydrogenation activity, e.g., Pt, and/or Pd, a lesser amount of dehydrogenation component is needed, e.g., in the range of 0.005 wt. % to 0.1 wt. %, based on the weight of the catalyst, such as 0.01 wt. % to 0.6 wt. %, or 0.01 wt. % to 0.05 wt. %. When the dehydrogenation component includes one or more metals of lesser dehydrogenation activity, e.g., one or more of Ga, In, Zn, Cu, Re, Mo, and W, a greater amount of dehydrogenation component is needed, e.g., in the range of 0.05 wt. % to 10 wt. %, based on the weight of the catalyst, such as 0.1 wt. % to 5 wt. %, or 0.5 wt. % to 2 wt. %.

The dehydrogenation component can be provided on, in, or proximate to the catalyst in any manner, for example by conventional methods such as impregnation or ion exchange. At least part of the dehydrogenation metal may also be present in the crystalline framework of the molecular sieve. For one representative catalyst, (i) the dehydrogenation component includes ≥95 wt. % of (A) Ga and/or (B) Zn, and (ii) the first molecular sieve component includes ≥95 wt. % of H-ZSM-5.

In certain aspects, the dehydrogenation component includes ≥99 wt. % of one or more of Ga, Zn, and In, and the molecular sieve component includes ≥99 wt. % of ZSM-5-type zeolite that has been impregnated with the dehydrogenation metal component and/or ion exchanged with the dehydrogenation metal component. For example, the catalyst can include Ga-impregnated and/or In-impregnated H-ZSM-5, Ga-exchanged and/or In-exchanged H-ZSM-5, H-gallosilicate of ZSM-5 type structure and H-galloaluminosilicate of ZSM-5 type structure. Optionally, the catalyst includes (i) tetrahedral aluminum and/or gallium, which is present in the zeolite framework or lattice, and/or (ii) octahedral gallium or indium, which is not present in the zeolite framework but present in the zeolite channels in close vicinity to the zeolitic protonic acid sites. While not wishing to be bound by any theory or model, the tetrahedral or framework Al and/or Ga is believed to contribute to acid function of the catalyst and octahedral or non-framework Ga and/or In is believed to contribute to the dehydrogenation function of the catalyst. Although typically the zeolite is impregnated or ion-exchanged with the dehydrogenation metal, other forms of zeolite can be used, such as H-galloaluminosilicate of ZSM-5 type structure having framework (tetrahedral) Si/Al and Si/Ga atomic ratios of about 10:1 to 100:1 and 15:1 to 150:1, respectively, and non-framework (octahedral) Ga of about 0.5 wt. % to 0 wt. %.

Particularly when the molecular sieve component comprises one or more aluminosilicate, the dehydrogenation component can include phosphorous, e.g., ≥1 wt. % phosphorus based on the weight of the dehydrogenation component, such as ≥10 wt. %, or ≥25 wt. %, or ≥50 wt. %, or ≥75 wt. %, or ≥90 wt. %, or ≥99 wt. %. It has been found that when the dehydrogenation component includes phosphorous, the catalyst becomes more resistant to deactivation (and increase aromatic hydrocarbon yield). When used, phosphorous can be included as a substituent for one or more metals of the molecular sieve. In such aspects, the amount of phosphorous is typically ≥1 wt. % based on the weight of the molecular sieve component. For example, when the molecular sieve component includes aluminosilicate, the phosphorous:aluminum atomic ratio can be in the range of from 0.01 to 1. Zeolite having a higher silica:alumina ratio can be utilized when a lower catalyst acidity is desired, e.g., in the range of from 44 to 100, such as from 50 to 80, or 55 to 75. When the catalyst includes aluminosilicate which includes phosphorous, the phosphorous : aluminum atomic ratio is typically in the range of from 0.01 to 0.5. For example, the catalyst can contain ≥10 wt. % of phosphorous-modified alumina, such as ≥15 wt. %, or in the range of from 10 wt. % to 20 wt. %.

Besides the molecular sieve component and dehydrogenation component, the catalyst can further include an optional matrix component, e.g., one or more inorganic binders. The amount of matrix component is not critical. When present, the amount of matrix component is typically in the range of 0.01 times the weight of the molecular sieve component to about 0.9 times the weight of the molecular sieve component, e.g., in the range of 0.02 to 0.8. The matrix component can include active materials, such as synthetic or naturally occurring zeolites. Alternatively, or in addition, the matrix component can include clays and/or oxides such as alumina, silica, silica-alumina, zirconia, titania, magnesia or mixtures of these and other oxides. The matrix component can include naturally occurring materials and/or materials in the form of gelatinous precipitates or gels including mixtures of silica and metal oxides. Clays may also be included with the oxide type binders to modify the mechanical properties of the catalyst or to assist in its manufacture.

Alternatively or in addition, the matrix component can include one or more substantially inactive materials. Inactive materials suitably serve as diluents to control the amount of conversion so that products may be obtained economically and in an orderly fashion without the need for employing other means for controlling the rate of reaction. Alternatively or in addition to any phosphorous added to or impregnated into the molecular sieve component, the matrix component can optionally include phosphorous, e.g., to lessen catalyst acidity. Those skilled in the art will appreciate that lessening catalyst acidity decreases the amount of catalyst coke produced during the catalytic conversion of the feed's light hydrocarbon to aromatic hydrocarbon. Suitable phosphorous-containing matrices are disclosed in U.S. Pat. No. 5,026,937, which is incorporated by reference herein in its entirety. The matrix component is optional. In certain aspects, the catalyst is substantially-free of matrix, e.g., contains ≤1 wt. % of matrix, such as ≤0.1 wt. %. In particular, the catalyst can be substantially free of binder, e.g., contains ≤1 wt. % of binder, such as ≤0.1 wt. %. For example, the catalyst's molecular sieve component can includes ≥95 wt. % of substantially binder-free molecular sieve, e.g., ≥95 wt. % and in particular small crystal H-ZSM-5.

The dehydrocyclization catalyst can be subjected to one or more treatments, e.g., a selectivation treatment to increase selectivity for producing desired aromatic hydrocarbon compounds such as para-xylene. For example, the selectivation can be carried out before introduction of the catalyst into the reactor and/or in-situ in the reactor, e.g., by contacting the catalyst with a selectivating agent, such as at least one organosilicon in a liquid carrier and subsequently calcining the catalyst at a temperature of 350° C. to 550° C. This selectivation procedure can be repeated two or more times and alters the diffusion characteristics of the catalyst such that the formation of para-xylene over other xylene isomers is favored. Such a selectivation process is described in detail in U.S. Pat. Nos. 5,633,417 and 5,675,047.

In particular aspects, the dehydrocyclization catalyst (Catalyst A) has a molecular sieve component which includes ≥90 wt. % of an aluminosilicate in hydrogen form, the aluminosilicate having a constraint index in the range of from 2-12 (e.g., phosphorous-modified H-ZSM-5) and a silica to alumina ratio in the range of from 50 to 80. For example, the molecular sieve component can include ≥95 wt. % of substantially binder-free, small crystal H-ZSM-5. For Catalyst A, the dehydrogenation component can include ≥90 wt. % of at least one oxide of Ga. The matrix component, when used, can include ≥75 wt. % of alumina, silica, and combinations thereof. Catalyst A optionally includes ≥1 wt. % phosphorus, e.g., in the form of phosphorous-modified H-ZSM-5 and/or by including phosphorous in the matrix component.

In other aspects the dehydrocyclization catalyst (Catalyst B) includes a molecular sieve component comprising ≥90 wt. % of an aluminosilicate in hydrogen form, the aluminosilicate having a constraint index in the range of from 2-12 (e.g., small crystal, H-ZSM-5). Typically, the dehydrocyclization catalyst of Catalyst B has (i) a silica:alumina ratio in the range of from 3 to 60, e.g., from 10 to 40, such as from 15 to 35, and (ii) ≤0.01 wt. % phosphorus. It is also typical for Catalyst B's dehydrogenation component to include ≥90 wt. % of (i) at least one oxide of Zn and/or (ii) at least one oxide of Ga, such as ≥95 wt. % of at least one oxide of Zn. The matrix component when used includes ≥90 wt. % of alumina, silica, and combinations thereof.

The specified dehydrocyclization catalysts can have any convenient form that is useful in the specified dehydrocyclization reaction. For example, the catalyst can have the form of a particulate, e.g., a plurality of catalyst particles having an average size ≤250 μm, e.g., in the range of 20 μm to 200 μm, and an average density in the range of from 0.6 g/cm$^3$ to 2 g/cm$^3$, e.g., in the range of from 0.9 g/cm$^3$ to 1.6 g/cm$^3$. Typically, the catalyst has a surface area, as measured by nitrogen physisorption, in the range of from 100 m$^2$/g to 600 m$^2$/g, e.g., in the range of from 200 m$^2$/g to 500 m$^2$/g. The catalyst can be located in one or more bed configurations, e.g., conventional bed configurations such as fixed bed, moving bed, ebullating bed, fluidized bed, etc. Any convenient reactor configuration can be used that is suitable for contacting the specified dehydrocyclization catalyst with the specified feed under the specified dehydrocyclization conditions for the specified average residence time in the reaction zone under the dehydrocyclization conditions. Conventional reactors are suitable, e.g., tubular reactors, including reverse-flow regenerative reactors, fluid-bed reactors, riser reactors, fixed bed reactors, etc. Any convenient method can be used for controlling the average residence time in the reaction zone of the specified dehydrocyclization catalyst under the specified dehydrocyclization conditions. Conventional methods can be used, e.g., adding and removing catalyst from a fluidized bed via catalyst inlet and outlet conduits, conveying the catalyst through a riser reactor, operating flow control valves to regulate the flow of feed and regenerating fluid through a tube reactor containing the dehydrocyclization catalyst, etc.

Representative Dehydrocyclization Reactions

A dehydrocyclization reaction is carried out to convert at least a portion of the olefinic product's $C_2$-$C_4$ hydrocarbon to aromatic hydrocarbon. The dehydrocyclization reaction can be carried out by exposing the feed to one or more beds containing a catalytically effective amount of at least one catalyst selected from among the specified dehydrocyclization catalysts. The reaction is carried out under conditions effective for catalytic dehydrocyclization. The catalyst's average residence time in the reaction zone is typically ≤90 seconds. Representative dehydrocyclization conditions include a temperature in range of from 400° C. to 800° C., e.g., 600° C. to 800° C.; a pressure ≥10 psia (68.9 kPa), e.g., 0 psig (101 kPa) to 300 psig (2170 kPa); and a space velocity (GHSV) ≥1100 hr$^{-1}$, e.g., in the range of from 1500 hr$^{-1}$ to 40,000 hr$^{-1}$. Typically, the catalyst has an average residence time in the reaction zone under the dehydrocyclization conditions of ≤60 seconds, e.g., in the range of from 0.001 second to 60 seconds, such as 0.01 second to 30 seconds. Those skilled in the art will appreciate that the specified temperature represents average temperatures across the catalyst bed. Average temperature is calculated by adding the bed's inlet temperature to the bed's outlet temperature, and then dividing the sum by 2. The specified pressure is not an average pressure. Instead, the specified pressure corresponds to that subsisting at the bed's inlet.

Typical process conditions include a temperature in range of from 630° C. to 750° C., e.g., 600° C. to 700° C.; a pressure in the range of from 20 psia (137.9 kPa) to 300 psig (2170 kPa), e.g., from 30 psia (207 kPa) to 80 psia (522 kPa); a space velocity (GHSV) in the range of from 2000 hr$^{-1}$ to 20,000 hr$^{-1}$, e.g., 2500 hr$^{-1}$ to 15,000 hr$^{-1}$. Typically, the dehydrocyclization catalyst has an average residence time in the reaction zone under the dehydrocyclization conditions of ≤45 seconds, e.g., ≤30 seconds, such as ≤10 seconds, or ≤1 second, or ≤0.1 second. For example, the catalyst can have an average residence time in the reaction zone under the dehydrocyclization conditions in the range of from 0.01 seconds to 10 seconds, e.g., 0.1 second to 10 seconds, such as 1 second to 10 seconds.

When carried out under the specified conditions, aromatic hydrocarbon selectivity is typically ≥30 wt. %, e.g., ≥40 wt. %, such as ≥50 wt. %, or ≥60 wt. %. Methane selectivity is typically ≤40 wt. %, e.g., ≤30 wt. %, such as ≤20 wt. %. $C_{2+}$ paraffin selectivity is typically ≤5 wt. %, e.g., ≤1 wt. %. $C_{2+}$ olefin selectivity is typically ≤20 wt. %, e.g., ≤10 wt. %. Advantageously, the process exhibits high conversion of olefinic hydrocarbon with low selectivity for methane over a wide range of conversion values. For example, the process can have an aromatic hydrocarbon selectivity ≥40 wt. % and a methane selectivity ≤40 wt. %. When the dehydrocyclization catalyst has an average residence time in the reaction zone under the dehydrocyclization conditions of ≤90 seconds, e.g., in the range of from 0.010 seconds to 30 seconds, olefinic hydrocarbon conversion (e.g., the $C_2$-$C_4$ olefinic hydrocarbon conversion, and in particular ethylene conversion) is typically ≥65 wt. %, e.g., ≥70 wt. %, such as ≥75 wt. %, or ≥80 wt. %, or in the range of from 65 wt. % to 95 wt. %. Typically, the aromatic product has a total aromatic hydrocarbon content of ≥5 wt. %, based on the weight of the aromatic product, such as ≥10 wt. %, or in the range of from 1 wt. % to 95 wt. %, or 10 wt. % to 75 wt. %. The process produces a desirable BTX product, typically having an increased yield of desirable xylene isomers and a decreased yield of less desirable $C_{11+}$ aromatic hydrocarbon in comparison with conventional processes. It can be desirable to alkylate at least a portion of the aromatic product to produce toluene and/or xylene, particularly when the aromatic product comprises benzene. Conventional alkylation processes (including successive alkylation processes) can be used, but the invention is not limited thereto. Examples of suitable alkylation processes are described in U.S. Pat. No. 6,642,426, and in U.S. Patent Application Publication No. 2015/0376088, these being incorporated by reference herein in their entireties.

Any convenient method can be employed for recovery of aromatic hydrocarbon from the aromatic product, including conventional methods such as boiling point separation, gravity separation, solvent extraction, etc. Non-aromatic $C_{2+}$ hydrocarbon is optionally recovered from the aromatic product, e.g., for recycle as a feed component. Methane and/or molecular hydrogen (e.g., tail gas) can also be recovered from the aromatic product, e.g., for storage, further processing, and/or use as a fuel.

Regeneration of the Dehydrocyclization Catalyst

In certain aspects, the dehydrocyclization reaction is carried out in a plurality of reactors, each reactor containing at least one bed of an active material selected from among the specified dehydrocyclization catalysts. Each of the reactors can be substantially the same as the others, e.g., having substantially the same bed configuration and containing substantially the same amount of substantially the same catalyst. Typically, one or more of the reactors in reaction (dehydrocyclization) mode while the other(s) are operated in regeneration mode, and vice versa. Continuous or semi-continuous operation can be carried out in each stage, e.g., by alternating reactors in sequence in reaction and regeneration modes.

Regeneration of the dehydrocyclization catalyst includes removing at least a portion of any accumulated deposits from the catalyst, e.g., coke and/or coke precursors. Typically, the dehydrocyclization catalyst is regenerated at an inlet temperature ≤700° C. Exceeding this temperature during regeneration has been found to result in catalyst de-alumination and/or loss of structure, leading to an undesirable loss of catalyst acidity. Catalyst regeneration for any of the specified catalysts is typically carried out using procedures which limit the maximum temperature to which the catalyst is exposed during regeneration to about 750° C., more typically to about 650° C. Conventional catalyst regeneration methods can be used, e.g., exposing the catalyst to at least one regeneration medium, e.g., an oxidant such as air or oxygen in air, for a time sufficient to remove at least a portion of the catalyst coke, but the invention is not limited thereto. Relatively uncommon regeneration media are within the scope of the invention, e.g., carbon dioxide, and/or molecular hydrogen. Typically, regeneration includes circulating a stream of at least one regeneration medium, particularly those which contain a limited amount of oxygen, since this limits the size of the exotherm where coke is burned off the catalyst. At the location where the regeneration medium enters the first reactor (most upstream, with respect to the flow of regeneration medium) e.g., at the reactor's inlet, the regeneration medium is typically exposed to a temperature ≤350° C., e.g., ≤325° C., such as ≤300° C. If needed, the oxidant content of the regenerating medium can be decreased to lessen the risk of exceeding the maximum temperature. Alternatively, or in addition, regeneration can be carried out by passing a stream of regeneration medium which comprises molecular hydrogen in proximity to the catalyst, e.g., for catalyst coke methanation.

Fluidized Bed Operation

Although fixed catalyst beds, moving catalyst beds, fluidized catalyst beds, ebullating catalyst beds, riser reactors, combinations thereof, etc., are all within the scope of the invention, certain aspects which include carrying out dehydrocyclization in one or more fluidized beds, will now be described in more detail. The invention is not limited to these aspects, and this description is not meant to foreclose the use of other catalyst bed configurations within the broader scope of the invention.

In fluidized bed aspects, the dehydrocyclization catalyst is typically in the form of a plurality of catalyst particles. The catalyst particles have an average catalyst particle residence time in the reaction zone of ≤90 seconds. The dehydrocyclization reaction is typically carried out in a reaction zone. Catalyst regeneration is carried out in a regeneration zone. During typical fluid bed operation, a portion of the dehydrocyclization catalyst is continuously transferred from the reaction zone to the regeneration zone, and regenerated dehydrocyclization catalyst is continuously transferred from the regeneration zone to the reaction zone. Besides being a convenient configuration for maintaining the specified average catalyst particle residence time in the reaction zone, a fluidized catalyst bed can be operated at a lesser pressure drop than fixed bed configurations of approximately the same capacity. Improved temperature control within the dehydrocyclization reaction zone is also typically achieved over fixed bed configurations, which desirably allows the bed to be more isothermal. Any convenient form of fluid bed reactor can be used for carrying out the dehydrocyclization reaction, including conventional fluid bed reactors such as those described (for a different purpose) in U.S. Pat. No. 4,751,338.

Referring to the FIGURE, at least a portion of the olefinic product is passed via conduit 1 for injection into reactor vessel 10 through one or more injectors proximate to a distributor grid 12. Additional feed or a lift gas (e.g., a light hydrocarbon gas) can be passed via conduit 14 through grid 12 to provide additional lift, as might be needed when a major amount of the feed is in the vapor phase upstream of the injection. Fluidization is effected in the bottom portion of the bed by upwardly flowing feed and any optional lift gas. Process conditions in reactor 10 can be controlled within the specified dehydrocyclization ranges, e.g., by adjusting feed temperature, catalyst temperature, catalyst circulation rate, (e.g., via valves $V_1$ and/or $V_2$), or by an indirect transfer of heat to or from conduit 16, which can be used for circulating a heat-transfer fluid.

The specified average catalyst particle residence time in the reaction zone is achieved by withdrawing catalyst from above grid 12 via conduit 7 provided with flow control valve $V_1$. The withdrawn catalyst is passed via air lift line 18 for catalyst regeneration in vessel 20, where combustible deposits (e.g., coke) are removed by oxidation with air or other regeneration gas. Should the combustion of these deposits provide insufficient heat to maintain the dehydrocyclization reaction in thermal balance, additional heat may be added via additional indirect heat transfer from the heat-transfer fluid of conduit 16. Alternatively or in addition, further catalyst heating during regeneration can be used, e.g., conveying the catalyst in line 18 with heated vapor (such as heated nitrogen, heated oxygen, heated air, etc.) and/or combusting a flue gas or other fuel stream in the regenerator, provided the catalyst does not exceed the temperature at which catalyst de-alumination and/or loss of structure would occur. It is also within the scope of the invention to conduct flue gas of regenerator 20 to reactor 10 (e.g., via line 14), which can lessen hydrocarbon partial pressure during dehydrocyclization and/or to decrease the amount of flue gas effluent conducted away from the process. Regenerated catalyst is returned to the reactor 10 via conduit 22 and valve $V_2$. To maintain the fluidized bed of reactor 10 in mass balance, the mass of the withdrawn catalyst is typically substantially the same as that of the replacement catalyst. In other words, $MFR_1$ can be substantially equal to the average mass flow rate of replacement catalyst added to the fluidized bed ($MFR_2$).

Although they are not shown, one or more cyclone particle separators can be used for removing entrained solids (e.g., catalyst fines) from the effluent of reactor 10, to produce the aromatic product. The aromatic product can be conducted to separation stage 30, for separating and recovering at least a portion of the aromatic product's aromatic hydrocarbon and optionally at least a portion of the aromatic product's non-aromatics. Non-aromatics can be recycled to the process, e.g., as feed and/or fuel components.

The dehydrocyclization catalyst in reactor 10 can have the form of a plurality of catalyst particles located in a turbulent fluidized bed, as indicated by the shaded region inside reactor 10. Typically, the bed has a density in the range of from 100 kg/m$^3$ to 500 kg/m$^3$ and a superficial fluid velocity ≥0.1 m/s, e.g., in the range of 0.1 m/s to 10 m/s, such as 0.3 m/s to 2 m/s. Size distribution of the dehydrocyclization catalyst is selected so that the catalyst will mix well throughout the bed. Large particles, e.g., those having a particle size greater than 250 μm, are generally avoided. Typically, ≥50 wt. % of the catalyst is in a particle size range of from about 1 μm to 150 μm, e.g., ≥75 wt. %, or ≥90 wt. % The dehydrocyclization typically has an average particle size in the range of about 20 μm to about 100 μm, e.g., 40 μm to 80 μm. It is also typical for the catalyst to have an average density in the range of from 0.6 g/cm$^3$ to 2 g/cm$^3$. The catalyst circulation rate is selected to achieve an average residence time for the dehydrocyclization catalyst in the bed of reactor 10 that is ≤ one hour, e.g., ≤30 minutes, such as ≤10 minutes, or ≤90 seconds, or ≤60 seconds, or ≤30 seconds, or ≤10 seconds, or ≤1 second. Relatively long residence times are within the scope of the invention, e.g., in the range of from 1 minute to 30 minutes, or from 1 minute to 10 minutes. Those skilled in the art will appreciate that an appropriate unit geometry and residence time can be selected to maintain the unit substantially in heat balance and to substantially maintain aromatic hydrocarbon yield over long run lengths. Relatively short residence times are also within the scope of the invention, e.g., in the range of from 0.1 seconds to 10 seconds. For an appropriately-sized reactor vessel 10 having a bed of volume $V_B$ of fluidized dehydrocyclization catalyst, the circulation rate can be adjusted in the desired range using valves $V_1$ and $V_2$. Typically, fresh or freshly-regenerated catalyst is added to the process to replace catalyst and/or catalyst fines removed from the process, e.g., during product recovery. This is an aid in maintaining $V_B$ substantially constant. In certain aspects, the dehydrocyclization catalyst is removed from (and added to) the fluid bed of reactor 10 at a rate >0.11 $V_B$/second, e.g., ≥0.017 $V_B$/second, such as ≥0.033 $V_B$/second, or ≥0.1 $V_B$/second, or ≥1 $V_B$/second, or in the range of from 0.03 $V_B$/second to 100 $V_B$/second, or 0.1 $V_B$/second to 10 $V_B$/second. Those skilled in the art will appreciate that riser reactors such as those used for carrying out fluidized catalytic cracking reactions may be a more appropriate form of fluidized catalyst reactor than that of the FIGURE when the catalyst particle residence time in the reaction zone is of relatively short duration, e.g., in the range of from 0.010 second to 0.1 second (equivalent to 10 $V_B$/second to 100 $V_B$/second). Typically, ≥90 wt. % of the replacement catalyst particles comprise regenerated catalyst particles. It is also typical for the freshly regenerated catalyst particles of conduit 22 to be at a greater temperature than the equilibrium dehydrocyclization catalyst in the fluid bed of reactor 10, but in other respects to have substantially the same physical, chemical, and compositional properties. The invention is not limited to aspects having one fluidized bed for carrying out the dehydrocyclization and one fluidized bed for carrying out the regeneration. Fluidized bed reactors systems having a plurality of fluidized beds for carrying out one or more of the specified dehydrocyclization reactions and/or one or more of the specified regenerations are within the scope of the invention, including those having a plurality of reactor and/or regenerator vessels. In particular, the dehydrocyclization is carried out in a staged fluidized bed reactor.

All patents, test procedures, and other documents cited herein, including priority documents, are fully incorporated by reference to the extent such disclosure is not inconsistent and for all jurisdictions in which such incorporation is permitted. Although certain aspects are described herein with particularity, other aspects will be apparent to and can be readily practiced by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside herein, including all features which would be treated as equivalents thereof by those skilled in the art to which this disclosure pertains. When lower and upper limits are specified, ranges from any lower limit to any upper limit are expressly within the scope of the invention. The term "comprising" is synonymous with the term "including". When a composition, an element or a group of components is preceded with the transitional phrase "comprising", the same composition or group of components is within transitional phrases "consisting essentially of," "consisting of," "selected from the group of consisting of," or "is" preceding the recitation of the composition, component, or components, and vice versa.

The invention claimed is:

1. A process for producing aromatic hydrocarbon, comprising:
    (a) providing a feed comprising ≥1 wt. % of methane;
    (b) producing an olefinic product by converting ≥10 wt. % of the feed's methane to $C_2$-$C_4$ olefinic hydrocarbon in a first conversion zone;
    (c) providing a dehydrocyclization catalyst having catalytic activity for hydrocarbon dehydrocyclization, wherein the dehydrocyclization catalyst includes a molecular sieve component and a dehydrogenation component;
    (d) producing an aromatic product by converting ≥10 wt. % of the olefinic product's $C_2$-$C_4$ olefinic hydrocarbon to aromatic hydrocarbon in the presence of the dehydrocyclization catalyst in a second conversion zone, wherein
        (i) the conversion is carried out under conversion conditions which include a temperature in the range of from 400° C. to 700° C., a pressure in the range of from 0 psig (101 kPa) to 300 psig (2170 kPa) and
        (ii) the dehydrocyclization catalyst has an average residence time in the conversion zone under the conversion conditions of ≤90 seconds; and
    (e) recovering at least a portion of the aromatic product's aromatic hydrocarbon.

2. The process of claim 1, wherein the feed comprises ≥10 wt. % of methane, and further comprises ≥5 wt. % of $C_{2+}$ hydrocarbon.

3. The process of claim 1, wherein step (b) is carried out by subjecting the feed to one or more of (i) methane pyrolysis conditions, (ii) oxidative coupling conditions, (iii) methane co-conversion conditions, and (iv) oxygenate synthesis followed by oxygenate dehydrogenation or oxygenate-to-olefin processing.

4. The process of claim 1, wherein (i) the dehydrocyclization catalyst includes ≥25 wt. % of the molecular sieve component and ≥0.05 wt. % of the dehydrogenation component, (ii) the molecular sieve component comprises ≥90 wt. % of one or more of MCM-22, ZSM-5, ZSM-11, ZSM-12, ZSM-22, ZSM-23, ZSM-35, and ZSM-48, and (iii) the dehydrogenation component comprises ≥90 wt. % of one or more of Ga, Zn, Cu, Re, Mo, W, La, Fe, Ag, Ni, In, Pt, and Pd.

5. The process of claim 1, wherein the dehydrocyclization catalyst comprises ≥50 wt. % of the molecular sieve component and ≥1 wt. % of the dehydrogenation component, (ii) the molecular sieve component comprises ≥95 wt. % of H-ZSM-5, and (iii) ≥90 wt. % the dehydrogenation component is Ga and/or Zn.

6. The process of claim 1, wherein the temperature is in the range of from 500° C. to 625° C., the pressure is in the range of from 30 psia (207 kPa) to 80 psia (522 kPa), the average residence time of the dehydrocyclization catalyst in the conversion zone under the conversion conditions is in the range of from 0.001 seconds to 60 seconds, and the conversion conditions further include a space velocity (GHSV) in the range of from 1100 hr$^{-1}$ to 40,000 hr$^{-1}$.

7. The process of claim 1, wherein the dehydrocyclization catalyst is in the form of a plurality of particles located in a turbulent bed, the bed having a density in the range of from 100 kg/m$^3$ to 500 kg/m$^3$ and a superficial fluid velocity in the range of 0.1 m/s to 10 m/s.

8. The process claim 7, wherein the dehydrocyclization catalyst particles have an average size ≤250 µm and an average density in the range of from 0.6 g/cm$^3$ to 2 g/cm$^3$.

9. The process of claim 8, wherein (i) the average residence time of the dehydrocyclization catalyst particles in the conversion zone is in the range of from 0.01 seconds to 30 seconds, the bed volume is $V_B$, and (iii) the average residence time is achieved by
(A) removing from the bed at least a portion of the dehydrocyclization catalyst particles at a rate in the range of 0.03 $V_B$/second to 100 $V_B$/second; and
(B) introducing into the bed replacement dehydrocyclization catalyst particles in an amount sufficient to maintain the bed volume $V_B$ substantially constant during the conversion, the replacement dehydrocyclization catalyst particles having catalytic activity for dehydrocyclization of the $C_{2+}$ non-aromatic hydrocarbon, an average size ≤250 µm, and an average density in the range of from 0.6 g/cm$^3$ to 2 g/cm$^3$.

10. The process of claim 9, further comprising at least partially regenerating the removed dehydrocyclization catalyst particles, wherein ≥50 wt. % of the replacement dehydrocyclization catalyst particles comprise regenerated catalyst particles.

11. A process for upgrading non-aromatic hydrocarbon, comprising:
(a) providing a feed comprising ≥5 wt. % of $C_2$-$C_4$ paraffinic hydrocarbon;
(b) producing an olefinic product by converting ≥10 wt. % of the feed's $C_2$-$C_4$ paraffinic hydrocarbon to $C_2$-$C_4$ olefinic hydrocarbon in a first conversion zone;
(c) providing a dehydrocyclization catalyst which includes (i) ≥25 wt. % of a molecular sieve component, the molecular sieve component comprising ≥90 wt. % of one or more of MCM-22, ZSM-5, ZSM-11, ZSM-12, ZSM-22, ZSM-23, ZSM-35, and ZSM-48, and (ii) ≥0.05 wt. % of a dehydrogenation component, the dehydrogenation component comprising ≥90 wt. % of one or more of Ga, Zn, Cu, Re, Mo, W, La, Fe, Ag, Pt, and Pd;
(d) producing an aromatic product by converting ≥10 wt. % of the olefinic product's $C_2$-$C_4$ olefinic hydrocarbon to aromatic hydrocarbon in the presence of the dehydrocyclization catalyst in a second conversion zone, wherein
(i) the conversion is carried out under conversion conditions which include a temperature in the range of from 400° C. to 700° C., a pressure in the range of from 0 psig (101 kPa) to 300 psig (2170 kPa) and
(ii) the dehydrocyclization catalyst has an average residence time in the conversion zone under the conversion conditions of ≤90 seconds; and
(e) recovering at least a portion of the aromatic product's aromatic hydrocarbon.

12. The process of claim 11, wherein the gaseous feed comprises 5 mole % to 50 mole % of ethane, 2 mole % to 40 mole % of propane, 0.1 mole % to 30 mole % of i-butane, 1 mole % to 30 mole % of n-butane, and 0.05 mole % to 25 mole % of i-pentane, and further comprises 0 mole % to 95 mole % of methane.

13. The process of claim 11, wherein step (b) is carried out by subjecting the feed to one or more of (i) hydrocarbon pyrolysis conditions, (ii) oxidative and/or non-oxidative coupling conditions, (iii) catalytic dehydrogenation conditions, (iv) catalytic and/or thermal hydrogen transfer conditions, and (v) $C_{2+}$ oxygenate synthesis followed by oxygenate dehydrogenation or oxygenate-to-olefin processing.

14. The process of claim 11, wherein the conversion of step (d) achieves an aromatic hydrocarbon selectivity ≥40 wt. % and a methane selectivity ≤40 wt. %.

15. The process of claim 11, wherein (i) the dehydrogenation component comprises ≥95 wt. % of (A) Ga and/or (B) Zn, and (ii) the molecular sieve component comprises ≥95 wt. % H-ZSM-5.

16. The process of claim 11, wherein during step (d) the average residence time is in the range of from 0.01 second to 30 seconds, the temperature in the range of from 500° C. to 625° C., the pressure in the range of from 30 psia (207 kPa) to 80 psia (522 kPa), and the GHSV is in the range of from 1500 hr$^{-1}$ to 40,000 hr$^{-1}$.

17. The process of claim 11, wherein the dehydrocyclization catalyst is in the form of a turbulent bed of a plurality of particles, the bed having a density in the range of from 100 kg/m$^3$ to 500 kg/m$^3$ and a superficial fluid velocity in the range of 0.1 m/s to 10 m/s.

18. The process claim 17, wherein particles have an average size ≤250 µm and an average density in the range of from 0.6 g/cm$^3$ to 2 g/cm$^3$.

19. The process of claim 18, wherein during step (d) the average residence time is in the range of from 0.1 second to 10 seconds, the bed volume is $V_B$, and the average residence time is achieved by:
(i) removing from the bed at least a portion of the dehydrocyclization catalyst particles at a rate in the range of 0.1 $V_B$/second to 10 $V_B$/second; and
(ii) introducing into the bed replacement catalyst particles in an amount sufficient to maintain the bed volume $V_B$ substantially constant during the conversion, the replacement catalyst particles having catalytic activity for dehydrocyclization of the $C_2$-$C_4$ paraffinic hydrocarbon, an average size ≤250 µm, and an average density in the range of from 0.6 g/cm$^3$ to 2 g/cm$^3$.

20. The process of claim 19, further comprising at least partially regenerating the removed dehydrocyclization catalyst particles, wherein ≥90 wt. % of the replacement catalyst particles comprise regenerated dehydrocyclization catalyst particles.

21. A process for producing aromatic hydrocarbon, comprising:
(a) providing a feed comprising ≥10 wt. % of $C_{5+}$ hydrocarbon;
(b) producing an olefinic product by converting ≥10 wt. % of the feed's hydrocarbon to $C_2$-$C_4$ olefinic hydrocarbon in a first conversion zone;
(c) providing a second conversion zone which includes a dehydrocyclization catalyst having catalytic activity for dehydrocyclization of the $C_2$-$C_4$ olefinic hydrocarbon,
(d) producing an aromatic product by converting ≥10 wt. % of the olefinic product's $C_2$-$C_4$ olefinic hydrocarbon to aromatic hydrocarbon in the presence of the dehydrocyclization catalyst in a second conversion zone, wherein
  (i) the conversion is carried out under conversion conditions which include a temperature in the range of from 400° C. to 700° C., a pressure in the range of from 0 psig (101 kPa) to 300 psig (2170 kPa) and
  (ii) the dehydrocyclization catalyst has an average residence time in the conversion zone under the conversion conditions of ≤90 seconds; and
(e) recovering at least a portion of the product's aromatic hydrocarbon.

22. The process of claim 21, wherein the feed has one or more of the following properties: a Conradson Carbon amount in the range of 5 wt. % to 40 wt. %, an API Gravity in the range of from −10° to 35°, and a boiling point at atmospheric pressure ≥340° C.

23. The process of claim 21, wherein the average residence time is in the range of from 0.01 second to 30 seconds, the temperature in the range of from 500° C. to 625° C., the pressure in the range of from 30 psia (207 kPa) to 80 psia (522 kPa), the GHSV is in the range of from 1500 hr$^{-1}$ to 40,000 hr$^{-1}$, the dehydrocyclization catalyst includes (i) ≥10 wt. % of a molecular sieve component, the molecular sieve component comprising ≥90 wt. % of one or more of MCM-22, ZSM-5, ZSM-11, ZSM-12, ZSM-22, ZSM-23, ZSM-35, and ZSM-48, and (ii) ≥0.005 wt. % of a dehydrogenation component, the dehydrogenation component comprising ≥90 wt. % of one or more of Ga, Zn, Cu, Re, Mo, W, La, Fe, Ag, Pt, and Pd.

24. The process of claim 21, wherein:
(i) the dehydrocyclization catalyst is substantially free of platinum,
(ii) the dehydrogenation component comprises ≥95 wt. % of (A) Ga and/or (B) Zn,
(iii) the molecular sieve component comprises ≥95 wt. % of H-ZSM-5;
(iv) the dehydrocyclization catalyst is in the form of a plurality of particles having an average size ≤250 μm and an average density in the range of from 0.6 g/cm$^3$ to 2 g/cm$^3$, the particles being located in a turbulent bed having volume $V_B$, a density in the range of from 100 kg/m$^3$ to 500 kg/m$^3$, and a superficial fluid velocity in the range of 0.1 m/s to 10 m/s;
(v) the average residence time is in the range of from 0.1 seconds to 10 seconds,
(iv) the average residence time is achieved by:
  (A) removing from the bed at least a portion of the dehydrocyclization catalyst particles at a rate in the range of 0.1 $V_B$/second to 10 $V_B$/second; and
  (B) introducing into the bed replacement catalyst particles in an amount sufficient to maintain the bed volume $V_B$ substantially constant during the conversion, the replacement catalyst particles having catalytic activity for dehydrocyclization of the feed's $C_{2+}$ non-aromatic hydrocarbon, an average size ≤250 μm, and an average density in the range of from 0.6 g/cm$^3$ to 2 g/cm$^3$.

25. The process of claim 21, wherein step (b) is carried out by subjecting the feed to one or more of (i) $C_{5+}$ hydrocarbon pyrolysis conditions and/or (ii) catalytic cracking conditions.

26. A process for producing aromatic hydrocarbon, comprising:
(a) providing a feed comprising ≥1 wt. % of paraffinic hydrocarbon;
(b) producing an olefinic product by converting ≥10 wt. % of the feed's paraffinic hydrocarbon to $C_2$-$C_4$ olefinic hydrocarbon in a first conversion zone, wherein the olefinic product includes at least portion of the $C_2$-$C_4$ olefinic hydrocarbon;
(c) providing a fluidized catalyst having catalytic activity for hydrocarbon dehydrocyclization,
(d) producing an aromatic product by converting ≥10 wt. % of the olefinic product's $C_2$-$C_4$ olefinic hydrocarbon to aromatic hydrocarbon in the presence of the fluidized catalyst in a second conversion zone, wherein:
  (i) the aromatic product includes at least a portion of the aromatic hydrocarbon and
  (ii) the conversion is carried out in a under turbulent fluidized bed conversion conditions which include a temperature in the range of from 400° C. to 700° C., a pressure in the range of from 0 psig (101 kPa) to 300 psig (2170 kPa); and
(e) recovering at least a portion of the aromatic product's aromatic hydrocarbon.

27. The process of claim 26, wherein the paraffinic hydrocarbon comprises methane and/or ethane, and the turbulent fluid bed conversion conditions include a superficial fluid velocity in the range of from 0.3 m/s to 2 m/s and a bed density in the range of from 100 kg/m$^3$ to 500 kg/m$^3$.

28. The process of claim 26, wherein the fluidized catalyst includes a molecular sieve component, the molecular sieve component comprising at least one aluminosilicate.

29. The process of claim 28, wherein the fluidized catalyst includes ≥1 wt. % phosphorous., the molecular sieve component includes ≥90 wt. % of at least one zeolite selected from the group consisting of MCM-22, ZSM-5, ZSM-11, ZSM-12, ZSM-22, ZSM-23, ZSM-35, and ZSM-48; and at least a portion of the phosphorous is present in the zeolite as a framework a substituent.

30. The process of claim 26, further comprising alkylating at least a portion of the aromatic product to produce toluene and/or xylene.

* * * * *